(12) United States Patent
Bollmann et al.

(10) Patent No.: US 9,095,634 B2
(45) Date of Patent: Aug. 4, 2015

(54) CONSTRUCTIVE FEATURE INTRODUCED IN TOOTHBRUSH HYGIENE DEVICE

(71) Applicant: TUPER S.A., São Bento do Sul (BR)

(72) Inventors: Frank Bollmann, São Bento do Sul (BR); Charles Adriano Duvoisin, São Bento do Sul (BR)

(73) Assignee: TUPER S.A., Sao Bento So Sul (BR)

( * ) Notice: Subject to any disclaimer, the term of this patent is extended or adjusted under 35 U.S.C. 154(b) by 0 days.

(21) Appl. No.: 14/181,220

(22) Filed: Feb. 14, 2014

(65) Prior Publication Data

US 2014/0234175 A1     Aug. 21, 2014

(30) Foreign Application Priority Data

Feb. 15, 2013    (BR) .......................... 202013003555 1

(51) Int. Cl.
| | |
|---|---|
| *B01D 11/02* | (2006.01) |
| *A61C 1/14* | (2006.01) |
| *B65D 73/00* | (2006.01) |
| *B65D 81/24* | (2006.01) |
| *A61L 2/18* | (2006.01) |
| *A46B 17/04* | (2006.01) |
| *A46B 17/06* | (2006.01) |

(52) U.S. Cl.
CPC . *A61L 2/18* (2013.01); *A46B 17/04* (2013.01); *A46B 17/065* (2013.01)

(58) Field of Classification Search
CPC .............. A61L 2/00; A61L 2/18; A46B 9/04; A46B 11/00

USPC ............ 433/49; 206/486, 209; 422/560, 565, 422/261, 292, 300; 13/21.1, 56, 146; 15/21.1, 56, 146

See application file for complete search history.

(56) References Cited

U.S. PATENT DOCUMENTS

| | | | |
|---|---|---|---|
| 1,448,231 A | 3/1923 | Morrison | |
| 4,585,119 A | 4/1986 | Boyington | |
| 5,522,497 A * | 6/1996 | Stacy | ........................ 206/209.1 |
| 2012/0138491 A1 | 6/2012 | Goss | |

FOREIGN PATENT DOCUMENTS

BR      MU8901827-3 A     5/2011

* cited by examiner

*Primary Examiner* — Monzer R Chorbaji
(74) *Attorney, Agent, or Firm* — Day Pitney LLP

(57) ABSTRACT

A toothbrush sanitation device includes a base with a container for immersing toothbrush bristles in a sanitizing, disinfecting or cleaning fluid and a lid. The base includes a perimeter flange with an annular protrusion and an annular cavity that are circular and concentric to the base and has a height that is 20% to 40% of the total height of the device. The container has a cylindrical inner wall with a rounded bottom and a conical outer wall which tapers toward an open end of the container, and has one or more level tags indications. The lid has a column and a fitting zone disposed in an open end adjacent to the column. An inner wall of the fitting zone is cylindrical, and the external taper of the container and the internal cylindricity of the fitting zone define a locking line.

4 Claims, 4 Drawing Sheets

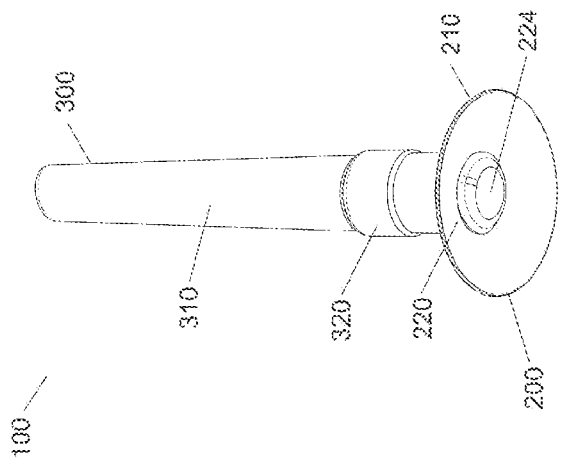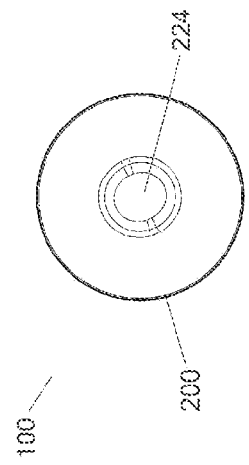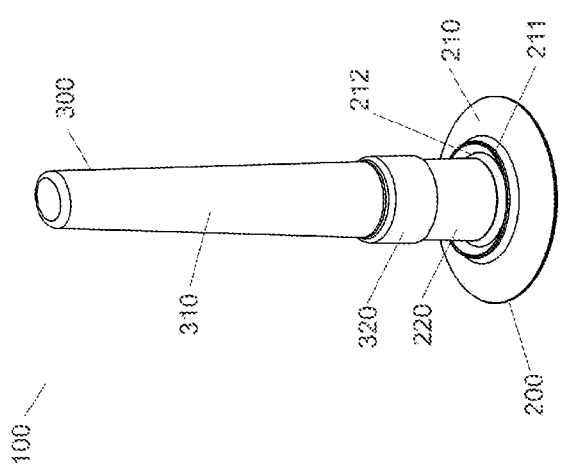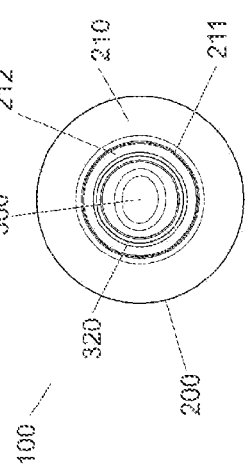

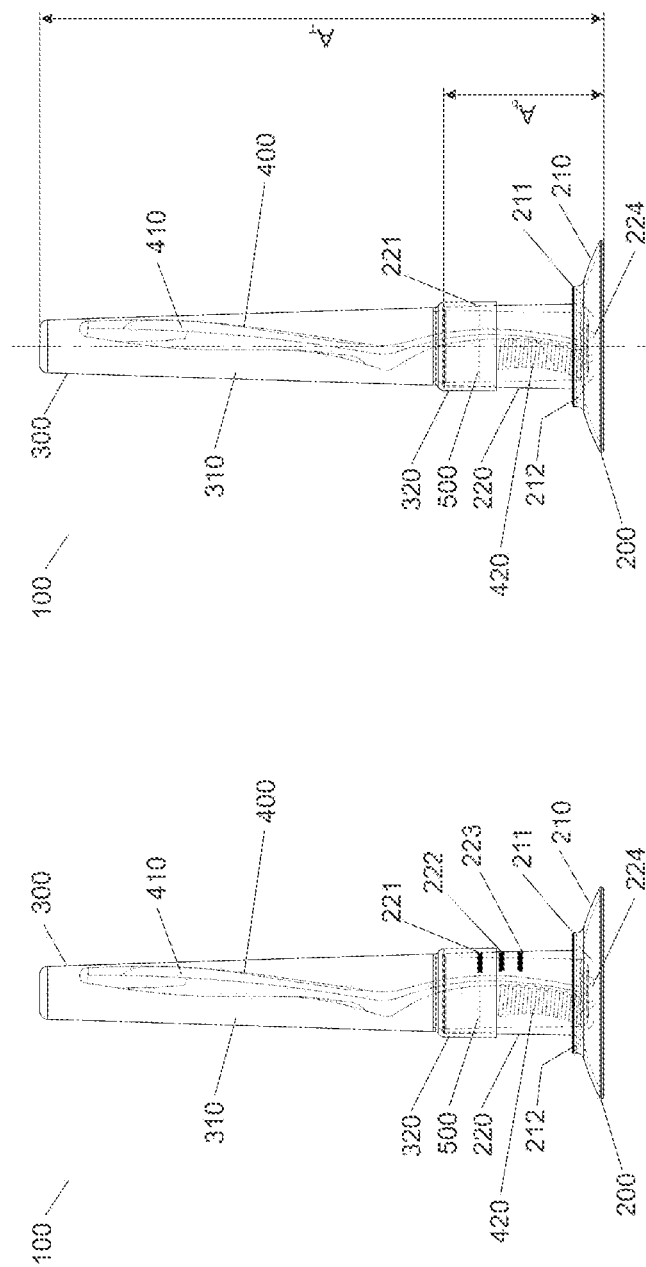

Figure 9:
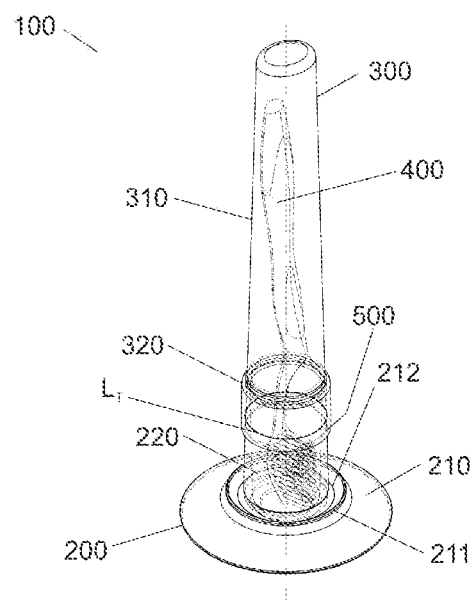

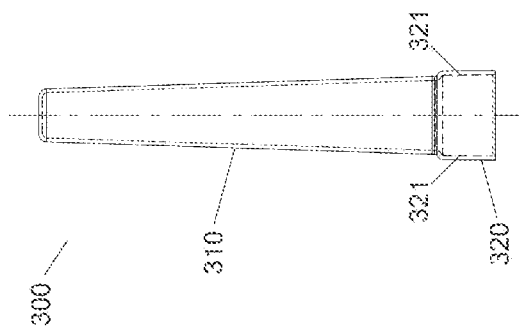
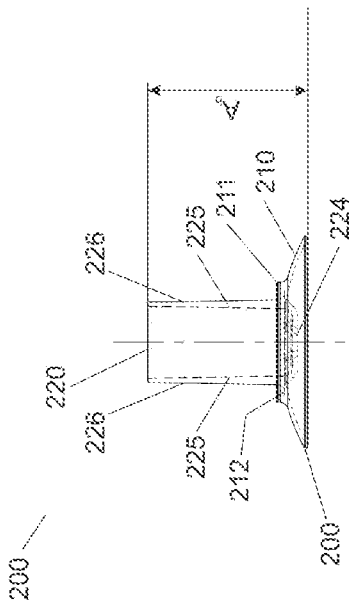

CONSTRUCTIVE FEATURE INTRODUCED IN TOOTHBRUSH HYGIENE DEVICE

CROSS-REFERENCE TO RELATED APPLICATIONS

This application claims priority to and the benefits of Brazilian Patent Application No. 20201300355 1, filed Feb. 15, 2013, the contents of which is incorporated by reference herein in its entirety.

BACKGROUND OF THE INVENTION

Field of Application

The present device belongs to the field of dental industry articles and oral hygiene, including devices for sanitation, disinfecting, support, and storage of brushes and other objects provided with grip and bristles.

(1) Field of the Invention

The object of the present description refers to a toothbrush sanitation device, wherein said device is intended for the sanitization and/or disinfection and/or cleaning of brushes, especially of the bristle head and the bristles themselves of toothbrushes by immersion of some specific areas of said brushes in a specific fluid contained in said device.

(2) Description of Related Art

Many configurations of devices having the nature described above, are known from the prior art, i.e. devices are known which propose the sanitization of toothbrushes by immersion of bristle of the brushes in an appropriate liquid for that purpose, contained in a container of the device.

An example of this is the solution disclosed by the Brazilin patent document number MU8901827-3, which refers to a "Constructive design for applying an antiseptic solution into the active end of instruments for tooth brushing". Said constructive design presents a solution for decontamination of bristles (7) of dental brushes (2), which are common in the market or specially designed for such arrangement. Thus, the document MU8901827-3 comprises two basic constructive possibilities, wherein it is possible to have a dispenser (1) independently of the brush (2), and in another embodiment, a dispenser (1) integrated into the grip (9) or the handle of the brush (2) itself. Said constructive design has some obvious disadvantages, particularly with regard to the enormous possibilities of contamination by accumulation of microorganisms in the fastening and sealing threads, both internal (4) and external (3). The narrow angles and the small access apertures make it difficult to sanitize the dispenser (1). The fact that the connection between the brush (2) and the dispenser (1), in one of the embodiments, is carried out by means of a thread (3, 4) also increases the possibility of fluid leakage at coupling, and makes the coupling itself difficult between the pieces, as the latter have distinct geometrical configurations, and, in the same embodiment, the grip of the brush (2) remains completely exposed to the external environment, thereby considerably increasing the risk of contamination of the bristle (5) by cross-contamination from the grip of the brush (2). Furthermore, the arrangement of an external thread (3) considerably increases the risk of injury in the lip region of the user. Finally, manufacturing costs are relatively high, when compared with the relatively low cost of toothbrushes.

U.S. Pat. No. 1,448,231 discloses a container for toothbrushes provided with a cylindrical body (5) with an open and chamfered end (6). A stopper or closure (7) has one of its ends (8) chamfered so that it matches the notch (6) of the body (5). The closed end of the closure or stopper (7) is formed with a rounded head or button (9) to facilitate griping of the stopper or closure (7), and it is also provided with a lid (10) having threads (11) at its lower end which mesh with threads (12) of the upper end of the body (5). Although the toothbrush grip (13) is covered entirely by the lid (10), the brush container of U.S. Pat. No. 1,448,231 presents varied possibilities of contamination from accumulation of microorganisms in the threads (11, 12), the double wall formed in the closure or stopper (7) and the inclined walls (6, 8) and grooves, which, of course, also makes it difficult to sanitize the entire container. The body (5) is long compared to the lid (10) which, in addition to the aforementioned problems, still makes access to the bottom itself difficult for the purpose of cleaning the container. Moreover, the complexity and, therefore, the manufacturing costs of the container of U.S. Pat. No. 1,448,231 are considerably higher, since it is a dual wall container with relative geometric complexity.

U.S. document No. U.S. Pat. No. 4,585,119 discloses toothbrush sanitation devices in which one of these devices (2) is provided with a plurality of containers (4), brackets (6), retainers (8), and lids (10). Each of the containers (4) comprises an elongated tube (14) closed in its lower portion (16), which retains an antiseptic solution (28), and open in its upper portion (18). The container (4) is also provided with internal protrusions (20), designed to squeeze the bristles (26) of the brush (12) in order to remove excess of antiseptic solution (28) upon withdrawal of the brush (12) from the container (4). As in the aforementioned documents of the prior art, the device of U.S. Pat. No. 4,585,119 propitiates contamination from accumulation of microorganisms in specific regions due to its geometric configuration, that is, both in the narrow (20) and adjacent portions of the same, which also makes cleaning of the container (4) more laborious as a whole. The container (4), although it does not entirely pack the brush, is long, which, in addition to the abovementioned problems, also makes access to its bottom difficult for the purpose of cleaning and makes it harder or generally prevents its use for shorter toothbrushes, for example, infant toothbrushes. Furthermore, the presence of narrowing or internal protuberances (20) of the device (2), in order to squeeze the bristles (26) while withdrawing the brush (12) from the container (4), erroneously induces the user not to promote rinsing of the brush (12) in tap water, giving the false impression of cleanliness because the bristles (26) have been compressed.

U.S. document No. US2012/0138491 discloses a device (110) for containing a toothbrush (150) comprising a housing (114) having an internal volume (118) for storing an antiseptic liquid (120), a horizontal filler line (122), a heavy base (130) and a lid (140), preferably from at least a rubber material. Said device (110) allows the contamination by accumulation of microorganisms in specific regions due to its geometric configuration and material, i.e. both in the heavy base (130) and the cover (140) made from rubber—porous material and microorganisms accumulator. The device (110) completely packs the brush (150), but it is long, which, in addition to the aforementioned problems, also makes access to the bottom thereof difficult for the purpose of cleaning and greatly hinders the removal especially of toothbrushes of shorter length, for example, infant toothbrushes.

Moreover, the level indication (horizontal filler line (122)) is unique and does not allow different controls of the level of liquid antiseptic (12) in the same housing (114).

BRIEF SUMMARY OF THE INVENTION

As can be deduced from the description above, the pertinent prior art discloses that there is space enough for improvements in toothbrush sanitation devices, especially with regard to the questions identified as deficient in the documents presented, i.e. an improved sanitation device can be imagined as being able to integrate the following features:

a) absence of corners, angles, sloped surfaces;
b) ease of opening and closing with guaranteed tightness;
c) ease of cleaning/sanitizing;
d) flexibility in use of brushes of various sizes in the same device with full grip protection;
e) possibility of controlling different levels of fluid;
f) positional stability and
g) prevention of leakage and spreading of fluid.

One of the objectives of the disclosed device is therefore to provide a toothbrush sanitation device according to the features of the claim 1. Changes in form or details related to the elements which compose the present device are depicted by the features of the dependent claims 2 and 3.

BRIEF DESCRIPTOIN OF THE SEVERAL VIEWS OF THE DRAWINGS

For a better understanding and visualizing of the object, this will now be described with reference to the accompanying figures, representing the functional improvement and the technical effect obtained by means of an exemplary embodiment, which is non-limiting in relation to the scope of the present invention, in which:

FIG. 1 presents a schematic view in right anterolateral perspective of a toothbrush sanitation device, which is object of the present invention;

FIG. 2 presents a schematic view in right inferolateral perspective of a toothbrush sanitation device, which is object of the present invention;

FIG. 3 presents a schematic top view of a toothbrush sanitation device, which is object of the present invention;

FIG. 4 presents a schematic bottom view of a toothbrush sanitation device, which is object of the present invention;

FIG. 5 presents a left side view of a toothbrush sanitation device, which is object of the present invention, with a toothbrush disposed in it;

FIG. 6 presents a left side view of a toothbrush sanitation device, which is object of the present invention, with a toothbrush disposed in it.

FIG. 7 presents a left side view of the base of a toothbrush sanitation device, which is object of the present invention;

FIG. 8 presents a left side view of the lid of a toothbrush sanitation device, which is object of the present invention;

FIG. 9 presents a view in right anterolateral perspective of a toothbrush sanitation device, which is object of the present invention, with a toothbrush disposed in it.

NUMERICAL REFERENCES TO THE FIGURES 100 toothbrush sanitation device
200 base
210 perimeter flange
211 annular protrusion
212 annular cavity
220 container
221 level tags/indications
222 level tags/indications
223 level tags/indications
224 rounded bottom
225 container inner wall
226 container outer wall
300 lid
310 column
320 fitting zone
321 inner wall of the fitting zone
400 toothbrush
410 grip
420 bristles
500 fluid
$A_b$ height of the base
$A_T$ total height
$L_T$ locking line

DETAILED DESCRIPTION OF THE INVENTION

FIGS. 1 and 2 show a schematic view in left and right anterolateral perspective, respectively, of a toothbrush sanitation device 100, which is object of this invention, and FIGS. 3 and 4 show the bottom and top schematic views, respectively, of a toothbrush sanitation device 100, which is object of this invention. FIG. 5 shows a left side view of a toothbrush sanitation device 100, which is object of the present invention, with a toothbrush 400 disposed in it, wherein the bristles 420 of the toothbrush 400 are fully immersed in fluid 500.

As can be inferred from FIGS. 1 and 5, the toothbrush sanitation device 100 basically consists of a base 200 and a lid 300, wherein said base 200 and said lid 300 can be made of any material suitable for this implementation.

In a preferred embodiment of the present invention, the base 200 is provided with a perimeter flange 210, an annular protrusion 211, an annular cavity 212, and a rounded bottom 220 of the container 224, and the lid 300 is provided with a column 310 and a fitting zone 320.

The perimeter flange 210 of the base 200 provides the first feature of positional stability of the toothbrush sanitation device 100, allowing the toothbrush sanitation device 100 to be constructed with sufficient height to allow use with toothbrushes 400 (see FIG. 5) of different sizes. Said perimeter flange 210 may have any shape, preferably circular shape, which allows linear contact of the base 200 with the surface on which the toothbrush sanitation device 100 is disposed.

The annular cavity 212 and the annular protrusion 211 adjacent thereto provide, respectively, containment and a bather for the portion of the fluid 500 that may eventually overflow from inside the base 200 when immersing the toothbrush 400 in the said fluid 500. In the case of this embodiment, both the annular cavity 212 and the annular protrusion 211 are circular and concentric to the base 200 and should preferably also have this format in case the perimeter flange 210 is not circular.

The container 220 of the base 200 provides a receptacle for containing the fluid 500 and is provided with several level tags/indications 221, 222, 223 to indicate to the user the correct fluid level, for example, different sizes and designs of toothbrush 400 to be immersed in said fluid 500. It should be noted that the sanitizing and/or disinfecting and/or cleaning of the toothbrush 400 preferentially occurs in the region of the bristles 420, wherein the level tags/indications 221, 222, 223 must be arranged in the container 220 so as to ensure the immersion of the bristles 420 and part of the grip 410 of the toothbrush (see FIG. 5).

It is important to mention that, as can be inferred from FIG. 6, the height of the base $A_b$ of the base 200 should represent between 20% and 40%, preferably between 25% and 35% of the total height $A_T$ of the toothbrush sanitation device 100, in order to ensure the second feature of positional stability of the toothbrush sanitation device 100 as a whole, even when the container 200 is empty. Thus, an optimum relation between the height of the base $A_b$ and the total height $A_T$ is represented by the following fraction:

$$\frac{A_b}{A_T} = 0,2 \ldots 0,4$$

It should be noted that both the features of dimensional stability of the toothbrush sanitation device 100 described above, that is, on the one hand the presence of a perimeter flange 210 of the base 200 and, on the other hand, the construction of a base 200 with a height of the base $A_b$ between 20% and 40% of the total height $A_T$, besides imparting to the toothbrush sanitation device 100 the above advantages, allow it to be made of lightweight materials and easy to clean, without compromising its positional stability such as, for example, polyamide (Nylon® with or without fibers), ABS (acrylonitrile butadiene styrene) and the like. Moreover, this feature increases the spectrum of possible manufacturing processes for the manufacture of the toothbrush sanitation device 100, which is object of this invention and greatly reduces manufacturing costs.

The use of synthetic material also allows the manufacture of toothbrush sanitation device 100 in various colors, for example for visual differentiation of devices 100. It is also advantageous to manufacture the toothbrush sanitation device 100, or at least the lid 300, in transparent plastic material, colored or not, to enable the external visual control of the level of fluid 500 contained in the container 220.

As can be inferred from FIG. 7, the container 220 of the base 200 is provided with container inner wall 225 essentially cylindrical and with rounded bottom 224 and rounded edges, which are features that allow, together with the relatively low height of the base $A_b$, an easy, fast and thorough cleaning and sanitation of the container 220 without the need for special tools or artifacts, and completely eliminates any regions of accumulation of microorganisms, viruses or food debris, enabling a high level of decontamination.

In this same embodiment, as can be inferred from FIGS. 1 to 6 and also from FIG. 8, the lid 300 is provided with a column 310 and a fitting zone 320 disposed in the open end of the lid 300 and adjacent the column 310.

The fitting zone 320 provides fitting and fixing by interference and friction between the lid 300 and base 200 in the region of the open end of the container 220. While the inner wall of the fitting zone 321 is cylindrical (see FIG. 8), the outer wall of the container 226 is tapered (see FIG. 7), tapering toward the open end of the container 220. Said external taper of the container 220, together with the internal roundness of the fitting zone 320, allows the hermetic closure of the toothbrush sanitation device 100, in which, while pressing the lid 300 on the base 200, a locking line $L_T$ is formed between the fitting zone 320 and the container 220 (see FIG. 9).

As can be inferred from the above description, the present invention discloses a constructive embodiment introduced in toothbrush sanitation device 100 able to remedy the deficiencies of the pertinent prior art, providing a toothbrush sanitation device 100 which includes the following features:

a) absence of corners, angles, sloped surfaces, especially in the containing region of fluid 500 and next to it, due to the inner wall of the container 225, the rounded bottom 224 and inner wall of the fitting zone 321;

b) ease of opening and closing with guaranteed tightness, due to the fitting and fixing by interference and friction between the lid 300 and the base 200, whose inner walls of the fitting zone 321 (cylindrical) and outer walls of the container 226 (conical) form a locking line $L_T$ between each other between the fitting zone 320 and the container 220;

c) ease of cleaning/sanitizing, due to the features mentioned in a) above, and because of the relatively low height of the base $A_b$;

d) flexibility in use of toothbrushes 400 of various sizes in the same device with full protection of the grip 410, due to the low center of gravity of the toothbrush sanitation device 100, as mentioned in c) above;

e) possibility to control different levels of fluid, due to the presence of one or more level tags/indications 221, 222, 223 and use of transparent plastic materials for making both the lid 300 and the base 200;

f) positional stability due to the presence of the perimetral flange 210 of the base 200 and the low center of gravity of the toothbrush sanitation device 100, as mentioned in c) above, and g) prevention of leakage and spreading of fluid, due to the presence of the annular cavity 212 and the annular protrusion 211.

It will be readily understood by those skilled in the art that modifications can be made to this invention without departing from the concepts set forth in the above description. These changes should be considered as comprised within the scope of the present invention. Accordingly, the particular embodiments described in detail above are only illustrative and exemplary and not limiting as to the scope of the present invention, to which the full scope of the appended claims and any and all equivalents thereof should be given.

What is claimed is:

1. A toothbrush sanitation device comprising:
    a base; and
    a lid;
    wherein said base comprises a container integrally extending upward therefrom, the container containing a fluid for at least one of sanitizing, disinfecting and cleaning by immersion of bristles of a toothbrush in said fluid,
    wherein the base has a perimeter flange, at least one annular protrusion, and at least one annular cavity, each of said perimeter flange, annular protrusion, and annular cavity being around the entire perimeter of the container, the annular cavity and perimeter flange configured to provide containment and a barrier for a portion of the fluid that overflows from inside the base;
    wherein the annular protrusion and the annular cavity are circular and concentric to the base and wherein the height of the base is 20% to 40% of the total height of the toothbrush sanitation device;
    wherein the container is provided with a container inner wall substantially cylindrical and with rounded bottom;
    wherein the container is provided with a conical container outer wall which tapers toward an open end of the container;
    wherein the container has one or more level tags or indicators;
    wherein said lid is provided with a column and a fitting zone disposed in the open end of the lid and adjacent to the column;
    wherein the inner wall of the fitting zone is cylindrical; and
    wherein the outer taper of the container and the internal cylindricity of the fitting zone determine, between each other, a locking line.

2. A toothbrush sanitation device as recited in claim 1, wherein at least one of the lid and the base are made of synthetic materials.

3. A toothbrush sanitation device as recited in claim 1, wherein at least one of the lid and the base are made of a transparent material.

4. A toothbrush sanitation device as recited in claim 1, wherein at least one of the lid and the base are made of a colored material.

\* \* \* \* \*